United States Patent [19]
Wozniak

[11] Patent Number: 5,955,071
[45] Date of Patent: Sep. 21, 1999

[54] FUNGAL SPECIES FOR THE BIOLOGICAL CONTROL OF THE SUGARBEET ROOT MAGGOT

[75] Inventor: Christopher A. Wozniak, Burtonsville, Md.

[73] Assignee: The United States of America as represented by the Secretary of Agriculture, Washington, D.C.

[21] Appl. No.: 09/120,347

[22] Filed: Jul. 21, 1998

[51] Int. Cl.⁶ .............................. A01N 63/00; C12N 1/20
[52] U.S. Cl. ..................... 424/93.5; 435/254.1; 435/911
[58] Field of Search ............................. 435/254.1, 259.1, 435/911; 424/93.5

[56] References Cited

U.S. PATENT DOCUMENTS 5,041,290  8/1991  Gindrat et al. ............................ 424/93

OTHER PUBLICATIONS

Smith, G.A., ARS Researchers Discover Another Potential Biopesticide Biological Project Explores Parasite *The Sugar Producer Magazine*, Mar. 1996, vol. 23, No. 3, pp. 14, 16 and 17.

*Primary Examiner*—Herbert J. Lilling
*Attorney, Agent, or Firm*—M. Howard Silverstein; Curtis P. Ribando; John D. Fado

[57] ABSTRACT

A new species of Syngliocladium, designated as *S. tetanopsis* Hodge, Humber and Wozniak, has been discovered which is pathogenic to the sugarbeet root maggot, *Tetanops myopaeformis* Röder. Spore formulations of this entomopathogen are useful for inciting a fatal mycoses in the sugarbeet root maggot. This species represents the only confirmed natural pathogen of this

FUNGAL SPECIES FOR THE BIOLOGICAL CONTROL OF THE SUGARBEET ROOT MAGGOT

BACKGROUND OF THE INVENTION

1. Field of the Invention

This invention relates to a method for controlling the sugarbeet root maggot by a fungal pathogen, *Syngliocladium tetanopsis*. This entomopathogen is a new species of the genus Syngliocladium, based upon spore, conidiophore and colony morphology.

2. Description of Prior Art

The sugarbeet root maggot, *Tetanops myopaeformis* Röder (Diptera:Otitidae) is a phytophagous insect, which in the larval stage causes severe economic loss to sugarbeet production in much of the United States. Primary host species are members of the Chenopodiaceae (i.e., *Beta vulgaris, Spinacia oleracea, Atriplex hortensis*). This insect causes significant yield losses in the Western United States where it has been erratically managed with granular preplant chemical insecticides (e.g., chlorpyrifos, terbufos, aldicarb) with varying degrees of success.

The aforementioned chemical insecticides are active for 60 days or less when incorporated into the soil at planting and have shown signs of being phytotoxic to sugarbeets. Moreover, prolonged use of chemical insecticides increase the potential for development of pesticide resistance in target species, non-target effects on beneficial species, pollution of groundwater and health hazards from human exposure.

No reports of natural pathogens infecting the sugarbeet root maggot exist in the literature. Efforts aimed at developing biological control agents for management of field infestations of sugarbeet root maggot have been minimal.

SUMMARY OF THE INVENTION

I have now discovered strains of a new virulent species of the entomopathogenic fungus *Syngliocladium tetanopsis* that are useful for selectively infecting and killing larvae and adults of the sugarbeet root maggot. Bioassays against lady beetles, lace wings, Colorado potato beetles, red and gray sunflower weevils, and tomato hornworms reveal that the fungus does not produce the same detrimental effects observed with the use of broad-spectrum, non-selective chemical insecticides. The fungus is readily cultured upon easily prepared, inexpensive medium and produces large numbers of propagules for use as inoculum in management of sugarbeet root maggots in agricultural situations.

In accordance with this discovery, it is an object of the invention to provide a biological alternative to chemical insecticides currently used for the control of sugarbeet root maggots.

It is a specific object of the invention to introduce new virulent isolates of *S. tetanopsis* that are useful for infecting and killing both larvae and adults of the sugarbeet root maggot.

A further specific object of the invention is to provide a formulation for control of the sugarbeet root maggot comprising an effective amount of a novel strain of *S. tetanopsis* together with a suitable carrier for application of the fungus to the locus of the pest and/or its plant host.

It is also a specific object of the invention to provide a method for the control of the sugarbeet root maggot on a host plant comprising applying a strain of *S. tetanopsis* to the vicinity of said plant.

Other objects and advantages of the invention will become readily apparent from the ensuing description.

DEPOSIT OF BIOLOGICAL MATERIAL

Purified isolates of *Syngliocladium tetanopsis* have been deposited in the U.S. Department of Agriculture, Agricultural Research Service Entomopathogenic Fungus (ARSEF) collection, Tower, Road, Ithaca, N.Y. 14853-2901, and also in the U.S. Department of Agriculture, Agricultural Research Service Culture Collection in Peoria, Ill., under the terms of the Budapest Treaty. Non-living specimens of the same isolates have been deposited in the Cornell University Plant Pathology Herbarium (CUP) in Ithaca, N.Y. Accession Numbers for these deposits are given below in Table I.

DETAILED DESCRIPTION OF THE INVENTION

The novel strains of the invention isolated from larvae of sugarbeet root maggots represent a new species of fungus, *Syngliocladium tetanopsis*. *S. tetanopsis* is entomogenous, mononematous or synnematous. Conidiogenous cells are frequently in monoverticillate whorls or pairs, (10.0--) 12.2 (--13.7) $\mu m \times 2.0$ $\mu m$, with a subcylindric base abruptly narrowing to a short, tapering neck; often strongly hooked or bent; producing ameroconidia enteroblastically in copious slime. Orange granules are often present on the hyphae and conidiogenous cells. Conidia are one-celled, subcylindric, (4.3-) 6.8 (--9.3)×(1.9--) 2.0 (--2.5) $\mu m$ (n=100). Chlamydospores are not observed. No teleomorph (sexual stage) is presently known for this conidial state.

The fungal propagules of *S. tetanopsis*, including the conidiospores and mycelia, can be mass-produced by any conventional means. For example, cultures of *S. tetanopsis* can be produced on oatmeal agar (OA: a filtered aqueous solution of 30 g/l rolled oats cooked for 30 min, 1.5% agar), modified oatmeal agar (mOA: an aqueous suspension of 30 g/l rolled oats cooked for 30 min., 1.2% agar, supplemented after autoclaving with 3 ml/l extra virgin olive oil and 30 mg/l cholesterol), malt extract agar (MEA, Difco[2]), and Sabouraud's dextrose agar with yeast extract (SDAY: 40 g/l dextrose; 20 g/l bacto-peptone; 20 g/l yeast extract; 1.5% agar). Cultivation of *S. tetanopsis* is conducted at temperatures in the range of 15–30° C., and preferably at 20–28° C. for a period of at least about 14, and preferably at least about 21 days after inoculation of the medium.

The conidiospores of *S. tetanopsis* lend themselves to formulation as liquid sprays, wettable powders, controlled-release granules and the like. For incorporation into liquid formulations suitable for field application, they can be suspended in water, saline, buffered solutions, or emulsions. These formulations can be applied directly to the pest, or alternatively applied to the soil, such as through a pressure sprayer, to incite an epizootic. The propagules can alternatively be combined with any conventional gel or solid carrier such as, sodium alginate, clay, vermiculite, $CaCO_3$, corn cob grits, etc. for application to the locus of the host plant or as a seed coating.

The actual concentration of conidiospores in a formulation is not particularly critical, and is a function of practical considerations such as the properties of the vehicle or carrier and the method and site of application. For purposes of formulation and application, an "effective amount" is defined to mean any quantity of conidiospores sufficient to infect the target insect and thereby induce the symptoms of the disease described below in Example 1. The expression "control of sugarbeet root maggot" is defined herein to mean that the level of damage to a host plant or to a plurality of host plants is significantly reduced as compared to an untreated control. It is understood that the reduced level of damage would typically be the direct result of a reduced number of viable insects in the locus of the host plants caused by an increase in insect mortality. Alternatively, the decrease in host plant damage could be the result of a reduced capacity of the insects to feed on the plants. It is also understood that reference herein to the sugarbeet root maggot is intended to include all stages of larvae as well as the adult. of course, it is expected that control of the larvae or adults in a field will also be reflected in reduced number of eggs and pupae in the field.

Following contact of first, second or third instar larvae or adults of the sugarbeet root maggot with conidiospores of the subject invention, a mycoses develops which kills the insect and allows sporulation of the fungus within and upon the cadaver. The larval cuticle becomes sclerotized and golden yellow to burnt orange in coloration prior to emergence of the fungus and sporulation. Stout white synnemata develop subsequently, and turn tan to pale orange with age. Spores are borne upon conidiogenous cells in monoverticillate whorls or pairs and serve to disseminate the fungus for further infection of suitable hosts.

EXAMPLE 1

Fungus-infected *T. myopaeformis* larvae were collected from sugarbeets in untreated border rows planted as buffer zones in a study of the efficacy of entomopathogenic nematodes as biocontrol agents conducted in Pembina Co., North Dakota. Dead or dying third instar larvae collected in the field were discolored yellow-tan with darkened cuticular lesions. When held in a moist chamber, white to yellow-orange tufts of sporulating mycelium erupted through the cuticle, and synnemata ultimately developed after 4–5 weeks at 25° C.

Table II shows the result of co-incubation of third instar larvae with $3 \times 10^5$ viable spores (positive FDA staining) per 120 g sterile sand in 9 cm dishes for seven days prior to removal to moistened filter paper discs. The control larvae were co-incubated with sterile saline (0.85% w/v) in sand and similarly observed for a 7-week period.

Co-incubation of third instar sugarbeet root maggot and varying numbers of conidiospores of *S. tetanopsis* show a dose-dependent infection and mortality as demonstrated in Table III. After removal from a sand-spore mix at 7 days (as above), larvae were rinsed and transferred to sterile filter paper discs moistened with distilled water. Larvae were observed for seven additional weeks and assessed for external signs of infection (i.e., sclerotization of cuticle, production of conidia) and mortality. Although confirmed mycoses (infection) lagged behind the mortality rate, it is clear from a comparison to the control (saline) treatment that the dose of fungal inoculum was correlated with mortality of third instar larvae. Application of condiospores to newly hatched first instar larvae supported upon a gellan gum (Gelrite, 0.5% v/v)-based medium similarly resulted in penetration of the larval cuticle by developing hyphae with subsequent production of conidiophores and fatal mycoses. However, sporulation was evident more quickly as compared to third instars (e.g., 14 days vs. 28 days after spore introduction).

TABLE I

*Syngliocladium* tetanopsis Isolate Accession Numbers

| Isolate | ARSEF | NRRL | CUP |
|---|---|---|---|
| FSt1A8-2294 | 5497[a] | 21853 | 64913 |
| FHi1A11-295 | 5577 | 21854 | — |
| FSt1A6-695 | 4972 | 30031 | 64915 |

[a]Holotype

TABLE II

% Mortality of Third Instar Sugarbeet Root Maggot Larvae[a]

| Days after incubation | ARSEF 5497 | ARSEF 5577 | Control |
|---|---|---|---|
| 23 | 86 | 92 | 9 |
| 53 | 98 | 96 | 34 |

[a]average of three experiments; n = 117 or 118.

TABLE III

Infection and Mortality of Third Instar Sugarbeet Root Maggot Larvae

| Days after incubation | Spores per plate | % Infection[a] | % Mortality[b] |
|---|---|---|---|
| 25 | 0 | 0 | 4 |
| 55 | 0 | 0 | 6 |
| 25 | $3 \times 10^3$ | 1 | 4 |
| 55 | $3 \times 10^3$ | 4 | 14 |
| 25 | $3 \times 10^4$ | 5 | 11 |
| 55 | $3 \times 10^4$ | 18 | 37 |
| 25 | $3 \times 10^5$ | 3 | 17 |
| 55 | $3 \times 10^5$ | 31 | 68 |
| 25 | $3 \times 10^6$ | 14 | 47 |
| 55 | $3 \times 10^6$ | 41 | 86 |

[a]strain ARSEF 5497; larval cadavers which failed to produce synnemata were not included in calculation summary
[b]Larvae which pupated were not included in calculation summary; n = 52 to 72 per treatment, average of two experiments.

I claim:

1. A purified isolate of *Syngliocladium tetanopsis* having the property of being infectious and fatal to larvae and adults of sugarbeet root maggot.

2. An isolate of claim 1 having all the identifying characteristics of NRRL 21853.

3. An isolate of claim 1 having all the identifying characteristics of NRRL 21854.

4. An isolate of claim 1 having all the identifying characteristics of NRRL 30031.

5. A method for controlling sugarbeet root maggot, comprising applying to the locus of larvae or adults thereof an effective amount of an isolate of *Syngliocladium tetanopsis* having the property of being infectious and fatal to said larvae and adults.

6. The method of claim 5 wherein said *Syngliocladium tetanopsis* is a strain having all the identifying characteristics of NRRL 21853.

7. The method of claim 5 wherein said *Syngliocladium tetanopsis* is a strain having all the identifying characteristics of NRRL 21854.

8. The method of claim 5 wherein said *Syngliocladium tetanopsis* is a strain having all the identifying characteristics of NRRL 30031.

* * * * *